(12) United States Patent
Huang et al.

(10) Patent No.: US 10,633,368 B2
(45) Date of Patent: Apr. 28, 2020

(54) VORICONAZOLE INTERMEDIATE AND VORICONAZOLE SYNTHESIS METHOD

(71) Applicant: ZHEJIANG HUAHAI PHARMACEUTICAL CO., LTD, Zhejiang (CN)

(72) Inventors: Hu Huang, Zhejiang (CN); Wenfeng Huang, Zhejiang (CN); Guoliang Tu, Zhejiang (CN); Jiegen Liu, Zhejiang (CN); Zhongming Xu, Zhejiang (CN); Qianghui Wu, Zhejiang (CN); Zhaoyang Meng, Zhejiang (CN); Yuling Fang, Zhejiang (CN)

(73) Assignee: ZHEJIANG HUAHAI PHARMACEUTICAL CO., LTD., Zhejiang (CN)

( * ) Notice: Subject to any disclaimer, the term of this patent is extended or adjusted under 35 U.S.C. 154(b) by 0 days.

(21) Appl. No.: 16/064,003

(22) PCT Filed: Jan. 16, 2017

(86) PCT No.: PCT/CN2017/071250
§ 371 (c)(1),
(2) Date: Jun. 20, 2018

(87) PCT Pub. No.: WO2017/108010
PCT Pub. Date: Jun. 29, 2017

(65) Prior Publication Data
US 2019/0002440 A1  Jan. 3, 2019

(30) Foreign Application Priority Data

Dec. 23, 2015  (CN) .................... 2015 1 0984590
Jan. 18, 2016  (CN) .................... 2016 1 0031465

(51) Int. Cl.
*C07D 403/06*  (2006.01)
*C07D 239/30*  (2006.01)

(52) U.S. Cl.
CPC ......... *C07D 403/06* (2013.01); *C07D 239/30* (2013.01)

(58) Field of Classification Search
CPC ............... C07D 403/06; C07D 239/38
USPC .................................. 544/313, 333
See application file for complete search history.

(56) References Cited

U.S. PATENT DOCUMENTS

2014/0350252 A1* 11/2014 Maheshwari ........ C07D 403/06
544/333
2019/0002440 A1  1/2019 Huang et al.

FOREIGN PATENT DOCUMENTS

| CN | 1195346 A | 10/1998 | |
|---|---|---|---|
| CN | 102344441 A | 2/2012 | |
| CN | 105503834 A | 4/2016 | |
| JP | 10-510549 A | 10/1998 | |
| WO | 1997/06160 A1 | 2/1997 | |
| WO | WO-2009084029 A2 * | 7/2009 | ........... C07D 403/06 |
| WO | 2012/114273 A1 | 8/2012 | |

OTHER PUBLICATIONS

Butters et al., Process Development of Voriconazole: A Novel Broad-Spectrum Triazole Antifungal Agent. Org Process Res Dev. Nov. 21, 2001;5(1):28-36.
March, Advanced Organic Chemistry, Reactions, Mechanisms, and Structure. Second Edition, 7th printing. McGraw-Hill International Book Company, Auckland. pp. 236-239, (1983).
Tong et al., Synthesis of a novel antifungal drug voriconazole. Central South Pharmacy. Apr. 2010;8(4):280-282.

* cited by examiner

*Primary Examiner* — Venkataraman Balasubramanian
(74) *Attorney, Agent, or Firm* — McCarter & English, LLP; Steven G. Davis; Wei Song

(57) ABSTRACT

Provided is a synthesis method for a voriconazole intermediate condensate as shown in formula II or an acid addition salt thereof. As shown in reaction formula 1, the product is prepared via compounds III and IV. The synthesis method adjusts the feeding means, and the reaction conditions are mild and controllable, thereby reducing the production of impurity A, avoiding the use of highly toxic metal lead, and eliminating the risk of highly toxic metal remaining in a drug. The product has a higher purity and significant industrial application value.

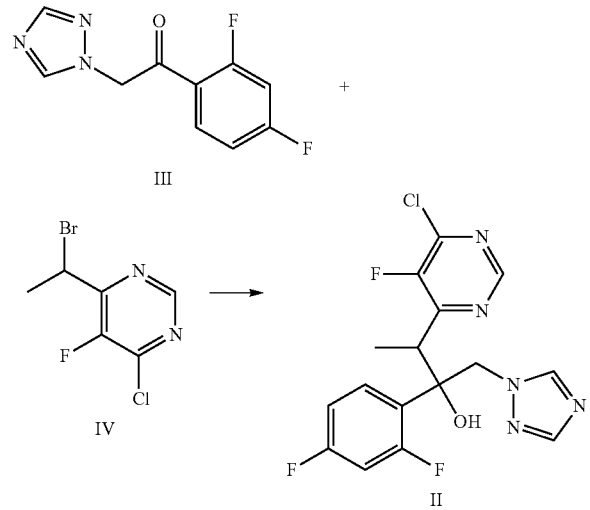

Reaction formula 1

17 Claims, No Drawings

VORICONAZOLE INTERMEDIATE AND VORICONAZOLE SYNTHESIS METHOD

CROSS-REFERENCE TO RELATED APPLICATIONS

This application is a U.S. national stage application filed under 35 U.S.C. § 371(c), of International Application No. PCT/CN2017/071250, filed on Jan. 16, 2017, which claims priority of Chinese Patent Application No. 201510984590.0, filed on Dec. 23, 2015, entitled "A synthesis method of Voriconazole intermediate", and Chinese Patent Application No. 201610031465.2, filed on Jan. 18, 2016, entitled "A synthesis method of Voriconazole intermediate". The entire contents of the aforementioned applications are incorporated herein by reference.

TECHNICAL FIELD

The present invention relates to a method for synthesizing an important intermediate condensation compound of Voriconazole, or a hydrochloride thereof, and a method for synthesizing Voriconazole.

BACKGROUND

Voriconazole (VRC, UK109496) is a novel antifungal agent synthesized by Pfizer Inc. USA on the basis of fluconazole, and is mainly used for patients with progressive, life-threatening immune damages. The market prospects of Voriconazole are broad because of its broad spectrum of antifungal activity, strong antibacterial efficacy and good safety, and because of the fast-growing demand for antifungal drugs in the domestic market.

The chemical name of Voriconazole is (2R,3S)-2-(2,4-difluorophenyl)-3-(5-fluoropyrimidin-4-yl)-1-(1H-1,2,4-triazol-1-yl)-2-butanol, and its structural formula is represented by formula I:

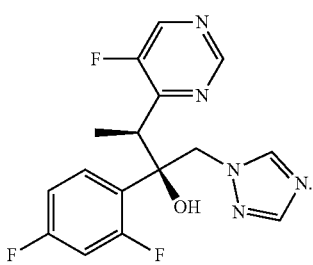

I

The chemical name of Voriconazole condensation compound, an important intermediate, is (2R,3S/2S,3R)-3-(6-chloro-5-fluoropyrimidin-4-yl)-2-(2,4-difluorophenyl)-1-(1H-1,2,4-triazol-1-yl)-2-butanol, and its structural formula is represented by formula II:

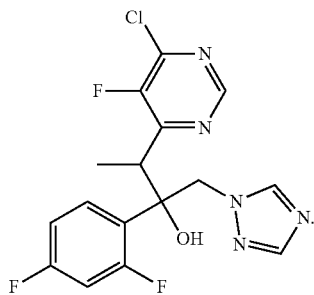

II

At present, the main synthesis method of the intermediate of formula II is shown in reaction scheme 1, comprising reacting 1-(2,4-difluorophenyl)-2-(1H-1,2,4-triazol-1-yl)ethanone of formula III with 4-(1-bromoethyl)-5-fluoro-6-chloropyrimidine of formula IV, in the presence of metal zinc, iodine or Lewis acid, and an aprotic organic solvent, with or without lead. The mechanism is that zinc powder first reacts with the compound of formula IV to form an organozinc reagent, which then reacts with the compound of formula III. The compounds of formula III and IV can be prepared using commercially available starting materials or methods disclosed in the prior art.

Reaction Scheme 1

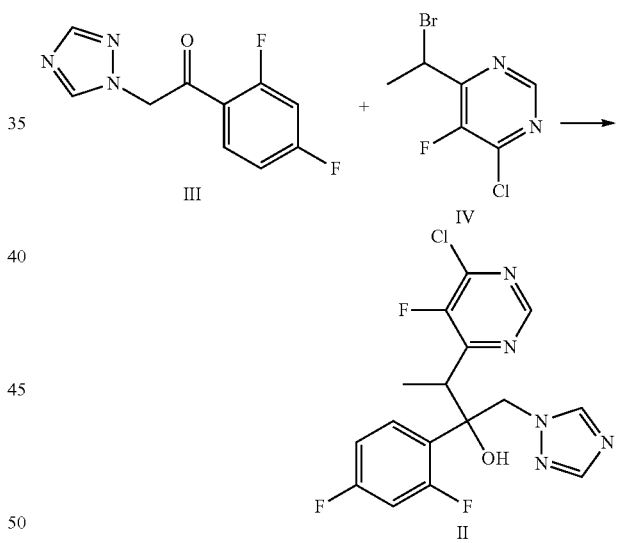

However, zinc powder is easily oxidized after contacting with air. This leads to a problem of initiation and activation during the preparation of the zinc reagent. Previous zinc powder-activating technology mainly involved lead powder. However, lead is a metal element with highly toxic and is strictly controlled in pharmaceutical process, and thus is unfavorable for large-scale industrial production. In addition, the charging mode has a great influence on the reaction during the synthesis of Voriconazole condensation compound. An improper charging mode method will lead to increased content of impurity A in the reaction and further affect the impurity removal of post-treatment and subsequent hydrogenation, which is extremely unfavorable for the reaction. Thus, it is important to strictly control charging mode for the reaction. The chemical name of impurity A is 3-(6-(1-(6-chloro-5-fluoropyrimidin-4-yl)ethyl)-5-fluoropyrimidin-4-yl)-2-(2,4-difluorophenyl)-1-(1H-1,2,4-triazol-1-yl)-2-butanol, and its structural formula is represented by formula V:

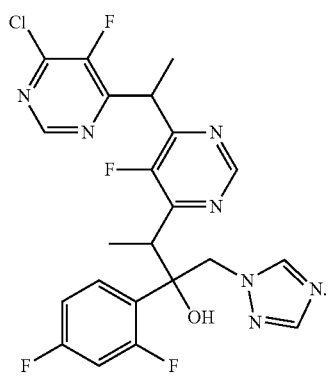

V

SUMMARY

The present invention provides a novel method for synthesizing an intermediate condensation compound of Voriconazole, represented by formula II, or an acid addition salt thereof. The method can effectively reduce the generation of impurity A by controlling the charging mode.

The present invention provides a novel method for synthesizing an intermediate condensation compound of formula II of Voriconazole or an acid addition salt thereof. The method comprises reacting a compound of formula III with a compound of formula IV in an aprotic organic solvent at a certain reaction temperature, in the presence of zinc and Lewis acid, with or without an activator, as shown in reaction scheme 1. The method includes following steps:

(a1) mixing the compound of formula III, zinc, and Lewis acid with the aprotic organic solvent to form a suspension;
(b1) mixing the compound of formula IV with the aprotic organic solvent, optionally in the presence of the activator to form a solution;
(e1) adding slowly the solution formed in step (b1) into the suspension formed in step (a1) and reacting to provide the intermediate condensation compound of formula II; and
(d1) optionally converting the intermediate condensation compound of formula II to the acid addition salt thereof;

or,
(a2) mixing the compound of formula III, zinc, and Lewis acid with the aprotic organic solvent to form a suspension;
(b2) mixing the compound of formula IV with the aprotic organic solvent to form a solution;
(c2) adding slowly the solution formed in step (b2) into the suspension formed in step (a2) and reacting, optionally in the presence of an activator to provide the intermediate condensation compound of formula II; and
(d2) optionally converting the intermediate condensation compound of formula II to the acid addition salt thereof;

or,
(a3) mixing the compound of formula III, the compound of formula IV, and Lewis acid with the aprotic organic solvent to form a suspension;
(b3) adding zinc into the suspension above, optionally in the presence of the activator, to provide the intermediate condensation compound of formula II; and
(c3) optionally converting the intermediate condensation compound of formula II to the acid addition salt thereof;

Reaction Scheme 1

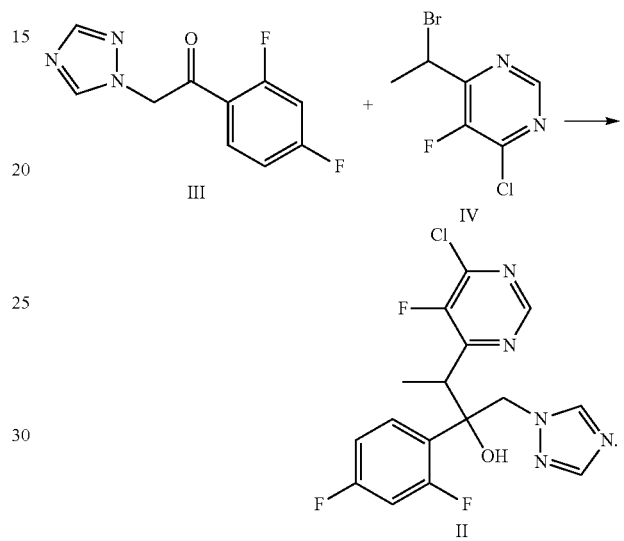

In a preferred embodiment of the present invention, the reaction is performed in the presence of an activator. In a further preferred embodiment of the present invention, the activator comprises iodine, bromine, dibromohydantoin, or 1,2-dibromoethane, preferably iodine and bromine.

In a preferred embodiment of the present invention, the weight ratio of activator to the compound of formula III is 0.05-2.0:1, preferably 0.1-0.2:1.

In a preferred embodiment of the present invention, the molar ratio of zinc, the compound of formula IV and the compound of formula III is 1-10:0.5-2.5:1, preferably 1.2-1.5:1.2-1.5:1.

In a preferred embodiment of the present invention, the reaction is performed as a temperature is 0-50° C., preferably 10-25° C.

In a preferred embodiment of the present invention, Lewis acid used in the reaction comprises chloride salts, bromide salts, iodide salts, aluminum oxide, titanium isopropoxide, titanium triisopropoxide chloride, boron trifluoride or trimethyl borate, preferably zinc chloride.

In a preferred embodiment of the present invention, the aprotic organic solvents used in step (a1) and step (b1), or step (a2) and step (b2) are the same.

In a preferred embodiment of the present invention, the aprotic organic solvent is $C_2$-$C_{10}$ aprotic organic solvent, preferably substituted or unsubstituted ether solvent, alkane solvent or aromatic hydrocarbon solvent, more preferably tetrahydrofuran.

The present invention also provides a method for synthesizing Voriconazole, comprising further reducing the intermediate condensation compound of formula II or the acid addition salt thereof, prepared according to the method of claim 1, to give the compound of formula VI, which is then resolved to give Voriconazole. The detailed synthesis route is as follows:

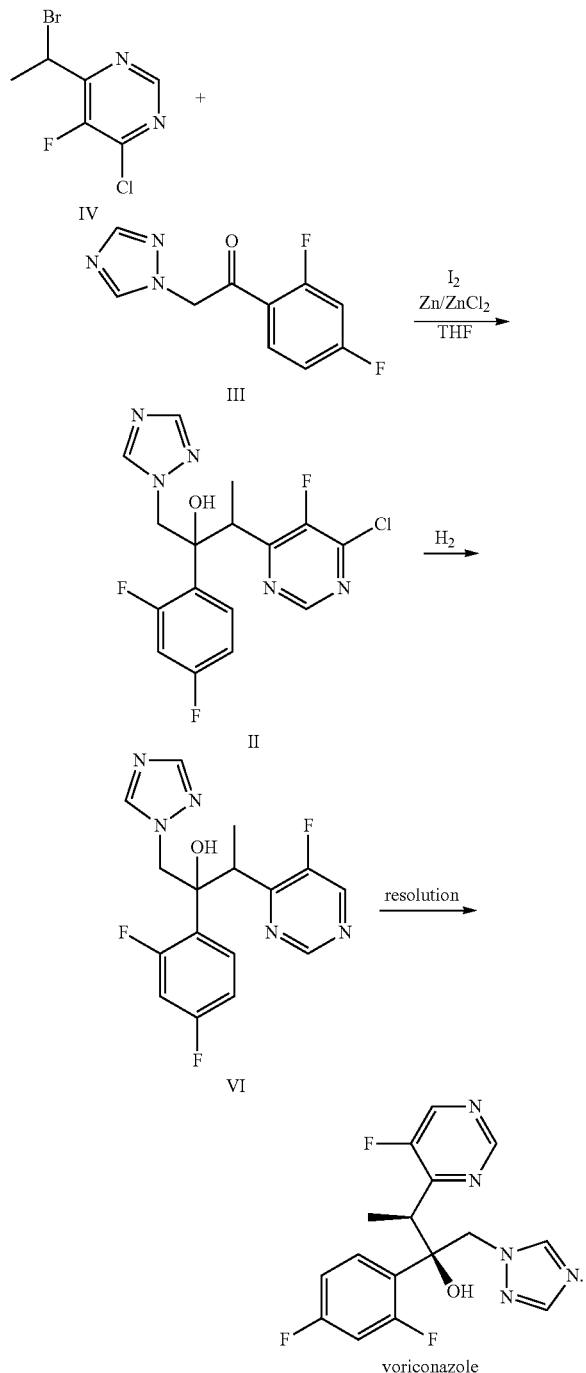

The technical solutions of the present invention have at least the following beneficial technical effects:
1. The reaction condition is moderate and controllable for generating an intermediate condensation compound of Voriconazole by adjusting the charging mode of the reaction;
2. The generation of impurity A can be reduced in the reaction above with an amount within 0.74%;
3. Lead powder is not involved in the above reaction, which eliminates the danger caused by the residue of toxic metal in a drug; and no separate activation treatment of zinc powder is required during the reaction.

DETAILED DESCRIPTION

Preparation of the Compound of Formula II and Acid Addition Salt Thereof: Examples 1-9

Example 1

THF (160 g) and compound III (20 g) were added into a flask under a nitrogen atmosphere at 20±5° C., stirred until dissolved to obtain a clarified solution. $ZnCl_2$ (13.6 g) and zinc powder (8.6 g) were added to the solution to form a suspension. A reaction was performed by dropwise adding a THF (160 g) solution of iodine (2.0 g) and compound IV (30 g) into the suspension. The reaction was carried out for 3 hours, and was terminated by dropwise adding a mixed solution of acetic acid (5.6 g) and water (160 mL). The resulting mixture was concentrated under reduced pressure, added with dichloromethane (208 g), water (100 mL) and acetic acid (5.8 g), stirred and then left to stand for layering. The aqueous layer was washed once with dichloromethane (110 g) and the organic phases were combined. The combined organic phase was washed with aqueous sodium bicarbonate solution, dried and concentrated, then dropwise added with hydrochloric acid to form a salt, which is crystallized to give a solid. The solid was dried in vacuum at 50° C. to give a crude product of (2R,3S/2S,3R)-3-(6-chloro-5-fluoropyrimidin-4-yl)-2-(2,4-difluorophenyl)-1-(1H-1,2,4-triazol-1-yl)-2-butanol hydrochloride (hydrochloride of the compound of formula II) (24.5 g, yield of 65.1%), with impurity A of 0.74%, as determined by liquid chromatography.

Example 2

THF (80 g) and compound III (10 g) were added into a flask under nitrogen atmosphere at 20±5° C., stirred until dissolved to obtain a clarified solution. Then $ZnCl_2$ (6.8 g) and zinc powder (4.3 g) were added to form a suspension. A reaction was performed by dropwise adding a THF (80 g) solution of iodine (2.0 g) and compound IV (15 g) into the suspension. The reaction was carried out for 3 hours. After that, the same post-treatment was performed as Example 1. A crude product of hydrochloride of compound of formula II was obtained (11.7 g, yield of 62.3%) with impurity A of 0.72%, as determined by liquid chromatography.

Example 3

THF (80 g) and compound III (10 g) were added into a flask under nitrogen atmosphere at 20±5° C., stirred until dissolved to obtain a clarified solution. Then $ZnCl_2$ (6.8 g) and zinc powder (4.3 g) were added to form a suspension. A reaction was performed by dropwise adding a THF (80 g) solution of iodine (1.0 g) and compound IV (11.8 g) into the suspension. The reaction was carried out for 3 hours. After that, the same post-treatment was performed as Example 1. A crude product of hydrochloride of compound of formula II was obtained (12.3 g, yield of 65.3%) with impurity A of 0.72%, as determined by liquid chromatography.

Example 4

THF (160 g) and compound III (10 g), compound IV (16.1 g), and $ZnCl_2$ (6.8 g) were successively added into a flask to form a suspension under nitrogen atmosphere at 15±5° C. Then, a reaction was performed by adding zinc powder (4.3 g) into the suspension. The reaction was carried out for 3 hours. After that, the same post-treatment was performed as Example 1. A crude product of hydrochloride of compound of formula II was obtained (12.1 g, yield of 64.4%) with impurity A of 0.68%, as determined by liquid chromatography.

Example 5

THF (80 g) and compound III (10 g) were added into a flask, stirred until dissolved to obtain a clarified solution, and $ZnCl_2$ (6.8 g) and zinc powder (4.3 g) were added to form a suspension under nitrogen atmosphere at 15±5° C. Then, a reaction was performed by dropwise adding a THF (80 g) solution of compound IV (15 g) into the suspension followed by adding iodine (1.0 g). The reaction was carried out for 3 hours. After that, the same post-treatment was performed as Example 1. A crude product of hydrochloride of compound of formula II was obtained (10.1 g, yield of 53.7%) with impurity A of 0.6%, as determined by liquid chromatography.

Example 6

THF (80 g) and compound III (10 g) were added into a flask under nitrogen atmosphere at 15±5° C., stirred until dissolved to obtain a clarified solution, and $ZnCl_2$ (6.8 g) and zinc powder (4.3 g) were added to form a suspension. Then, a reaction was performed by dropwise adding a THF (80 g) solution of dibromohydantoin (1.3 g) and compound IV (16.1 g) into the suspension. The reaction was carried out for 3 hours. After that, the same post-treatment was performed as Example 1. A crude product of hydrochloride of compound of formula II was obtained (9.4 g, yield of 50.1%) with impurity A of 0.5%, as determined by liquid chromatography.

Example 7

THF (80 g) and compound III (10 g) were added into a flask under nitrogen atmosphere at 15±5° C., stirred until dissolved to obtain a clarified solution, and $ZnCl_2$ (6.8 g) and zinc powder (4.3 g) were added to form a suspension. Then, a reaction was performed by dropwise adding a THF (80 g) solution of compound IV (16.1 g) into the suspension followed by adding dibromohydantoin (1.3 g). The reaction was carried out for 3 hours. After that, the same post-treatment was performed as Example 1. A crude product of hydrochloride of compound of formula II was obtained (10.4 g, yield of 55.3%) with impurity A of 1.3%, as determined by liquid chromatography.

Example 8

THF (80 g) and compound III (10 g) were added into a flask, stirred until dissolved to obtain a clarified solution, and $ZnCl_2$ (6.8 g) and zinc powder (4.3 g) were added to form a suspension under nitrogen atmosphere at 15±5° C. Then, a reaction was performed by dropwise adding a THF (80 g) solution of bromine (1.0 g) and compound IV (16.1 g) into the suspension. The reaction was carried out for 3 hours. After that, the same post-treatment was performed as Example 1. A crude product of hydrochloride of compound of formula II was obtained (11.4 g, yield of 60.7%) with impurity A of 0.63%, as determined by liquid chromatography.

Example 9

THF (80 g) and compound III (10 g) were added into a flask under nitrogen atmosphere at 15±5° C., stirred until dissolved to obtain a clarified solution, and $ZnCl_2$ (6.8 g) and zinc powder (4.3 g) were added to form a suspension. Then, a reaction was performed by dropwise adding a THF (80 g) solution of compound IV (15 g) into the suspension followed by adding bromine (1.3 g). The reaction was carried out for 3 hours. After that, the same post-treatment was performed as Example 1. A crude product of hydrochloride of compound of formula II was obtained (11.1 g, yield of 59.1%) with impurity A of 0.5%, as determined by liquid chromatography.

Comparative Example

THF (100 g) zinc powder (8.6 g) and $ZnCl_2$ (13.6 g) was added into a flask under nitrogen atmosphere at 20±5° C., and stirred to form a suspension. Iodine (1.8 g) dissolved in THF (60 g) was slowly added into the suspension over 10 minutes to obtain a mixture. Then, a reaction was performed by slowly adding a mixture of compound III (20 g), compound IV (30 g), and iodine (0.2 g) dissolved in tetrahydrofuran (160 g) into the above mixture. The reaction was carried out for 3 hours. After that, the same post-treatment was performed as Example 1. A crude product of hydrochloride of compound of formula II was obtained (23.2 g, yield of 62%) with impurity A of 9%, as determined by liquid chromatography.

Example 10: Preparation of Compound of Formula VI

Methanol (69 g), the compound of formula II (10 g), crystalline sodium acetate (7.6 g) and palladium on carbon 7% (wet basis) (0.7 g) were added into a hydrogenation reactor. The reactor was replaced with nitrogen three times, added with nitrogen gas to 0.4 MPa, and then pressurized for 5 minutes to check for gas leakage. The reactor was further replaced with hydrogen three times, then added with hydrogen until the pressure reached 0.3 MPa. The temperature was controlled to 25-30° C. The reaction was stirred for 3-5 hours until no pressure drop occurred within 30 minutes (the pressure was increased to 0.3 MPa when it was reduced to 0.2 MPa). The reaction mixture was concentrated under reduced pressure after being discharged, added with dichloromethane (40 g) and water (24 g), followed by extraction and layering. The aqueous layer was further extracted twice with dichloromethane (40 g), and the organic phases were combined. Water (30 g) was added into the combined organic phase, and pH of the mixture was adjusted to 9-11 by the dropwise addition of sodium hydroxide solution followed by layering. The organic phase was dried with anhydrous magnesium sulfate and filtered. The filtrate was concentrated under reduced pressure to give a concentrate. Then, the resulting concentrate was added with isopropyl alcohol (19 g), stirred and heated to reflux for 20 minutes. Then, the temperature was lowered to 20-30° C. at which the reaction was stirred for 1 hour, and then lowered to 0° C. at which the reaction was stirred for 2 hours to separate out a large amount of precipitate. The resulting mixture was filtered and the filter cake was dried in vacuum to give the compound of formula VI (7.1 g, 85%).

Example 11: Preparation of Voriconazole

Acetone (58.5 g), methanol (19.5 g), the compound of formula VI (3.5 g) were added into a flask, stirred until dissolved to obtain a clarified solution, then added with L-camphorsulfonic acid (2.3 g), heated to reflux and kept for 30 minutes. The reaction mixture was cooled to 30° C. After the temperature being cooled to 30° C., the reaction mixture was slowly cooled to 20° C. over 1 hour at which the mixture was stirred for 2 hours. Then, the resulting mixture was filtered and the filter cake was dried in vacuum to give the camphorsulfonate salt of the resolution product of Voriconazole, i.e., L-camphoranesulfonate salt of (2R,3S)-2-(2,4-difluorophenyl)-3-(5-fluoropyrimidin-4-yl)-1-(1H-1,2,4-triazol-1-yl)-2-butanol (1.9 g, 32%). The resulting L-camphoranesulfonate salt of Voriconazole was dissolved in a dichloromethane solvent, and allowed to free by dropwise adding sodium bicarbonate to obtain Voriconazole.

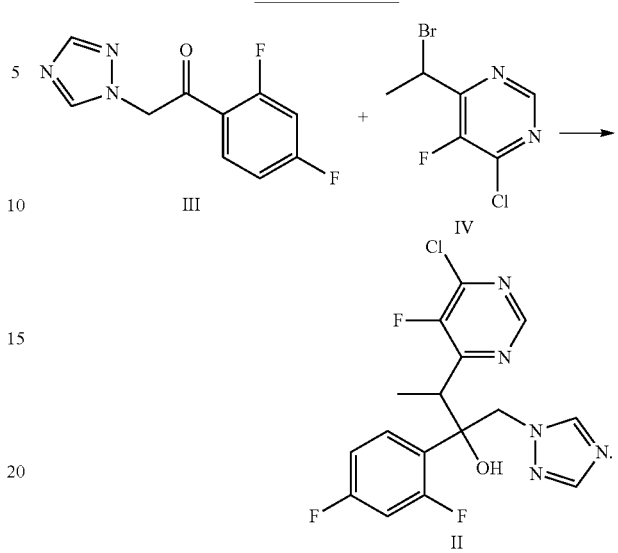

Reaction Scheme 1

What is claimed is:

1. A method for synthesizing an important intermediate condensation compound of formula II of Voriconazole or an acid addition salt thereof, comprising reacting a compound of formula III with a compound of formula IV in an aprotic organic solvent at a certain reaction temperature, in the presence of zinc and a Lewis acid, with or without an activator, as shown in a reaction scheme 1, wherein the method comprises following steps:
   (a1) mixing the compound of formula III, zinc and the Lewis acid with the aprotic organic solvent to form a suspension;
   (b1) mixing the compound of formula IV with the aprotic organic solvent, optionally in the presence of the activator, to form a solution;
   (c1) adding slowly the solution formed in step (b1) into the suspension formed in step (a1) and reacting to provide the intermediate condensation compound of formula II; and
   (d1) optionally converting the intermediate condensation compound of formula II to an acid addition salt thereof; or,
   (a2) mixing the compound of formula III, zinc and the Lewis acid with the aprotic organic solvent to form a suspension;
   (b2) mixing the compound of formula IV with the aprotic organic solvent to form a solution;
   (c2) adding slowly the solution formed in step (b2) into the suspension formed in step (a2), optionally in the presence of the activator and reacting to provide the intermediate condensation compound of formula II; and
   (d2) optionally converting the intermediate condensation compound of formula II to an acid addition salt thereof; or,
   (a3) mixing the compound of formula III, the compound of formula IV, and the Lewis acid with the aprotic organic solvent to form a suspension;
   (b3) adding zinc into the suspension, optionally in the presence of the activator, to provide the intermediate condensation compound of formula II; and
   (c3) optionally converting the intermediate condensation compound of formula II to an acid addition salt thereof;

2. The method according to claim 1, wherein the reaction is performed in the presence of the activator.

3. The method according to claim 2, wherein the activator comprises iodine, bromine, dibromohydantoin, or 1,2-dibromoethane.

4. The method according to claim 2, wherein the weight ratio of the activator to the compound of formula III is 0.05-2.0:1.

5. The method according to claim 1, wherein the molar ratio of zinc, the compound of formula IV and the compound of formula III is 1-10:0.5-2.5:1.

6. The method according to claim 1, wherein the reaction is performed at a temperature of 0-50° C.

7. The method according to claim 1, wherein the Lewis acid used in the reaction comprises chloride salts, bromide salts, iodide salts, aluminum oxide, titanium isopropoxide, titanium triisopropoxide chloride, boron trifluoride, or trimethyl borate.

8. The method according to claim 1, wherein the aprotic organic solvents used in step (a1) and step (b1), or step (a2) and step (b2) are the same.

9. The method according to claim 1, wherein the aprotic organic solvent is $C_2$-$C_{10}$ aprotic organic solvent.

10. A method for synthesizing Voriconazole, comprising further reducing an intermediate condensation compound of formula II or an acid addition salt thereof, prepared by the method according to claim 1, to give a compound of formula VI; and resolving the compound of formula VI to give Voriconazole, according to a following synthesis route:

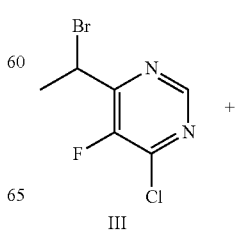

III

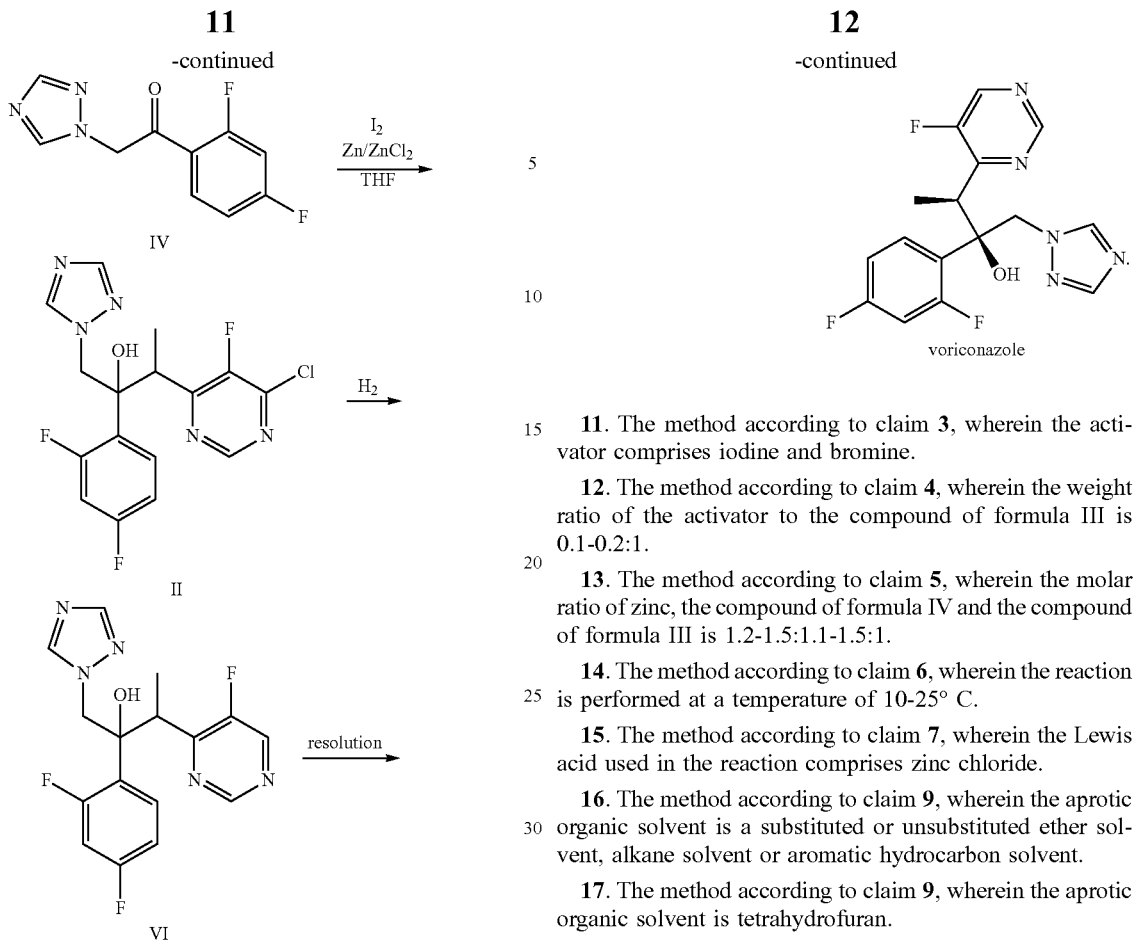

voriconazole

11. The method according to claim 3, wherein the activator comprises iodine and bromine.

12. The method according to claim 4, wherein the weight ratio of the activator to the compound of formula III is 0.1-0.2:1.

13. The method according to claim 5, wherein the molar ratio of zinc, the compound of formula IV and the compound of formula III is 1.2-1.5:1.1-1.5:1.

14. The method according to claim 6, wherein the reaction is performed at a temperature of 10-25° C.

15. The method according to claim 7, wherein the Lewis acid used in the reaction comprises zinc chloride.

16. The method according to claim 9, wherein the aprotic organic solvent is a substituted or unsubstituted ether solvent, alkane solvent or aromatic hydrocarbon solvent.

17. The method according to claim 9, wherein the aprotic organic solvent is tetrahydrofuran.

* * * * *

UNITED STATES PATENT AND TRADEMARK OFFICE
CERTIFICATE OF CORRECTION

PATENT NO. : 10,633,368 B2
APPLICATION NO. : 16/064003
DATED : April 28, 2020
INVENTOR(S) : Hu Huang et al.

Page 1 of 1

It is certified that error appears in the above-identified patent and that said Letters Patent is hereby corrected as shown below:

In the Claims

At Column 10, Claim 10, Lines 57-66, replace " 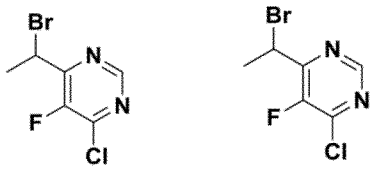 " with -- --;

At Column 11, Claim 10, Lines 1-8, replace " 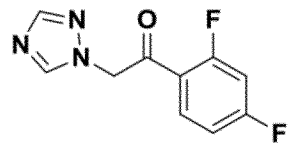 " with -- 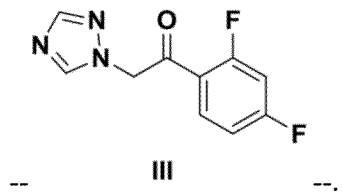 --.

Signed and Sealed this
Ninth Day of June, 2020

Andrei Iancu
*Director of the United States Patent and Trademark Office*